US009903866B2

(12) United States Patent
Barbosa (10) Patent No.: US 9,903,866 B2
(45) Date of Patent: Feb. 27, 2018

(54) PORTABLE DEVICES FOR DETECTION OF ANTIBODIES AGAINST THERAPEUTIC DRUGS

(71) Applicant: Maria D. F. S. Barbosa, Philadelphia, PA (US)

(72) Inventor: Maria D. F. S. Barbosa, Philadelphia, PA (US)

(73) Assignee: ConquerAb Inc., Philadelphia, PA (US)

( * ) Notice: Subject to any disclaimer, the term of this patent is extended or adjusted under 35 U.S.C. 154(b) by 0 days.

(21) Appl. No.: 15/376,775

(22) Filed: Dec. 13, 2016

(65) Prior Publication Data

US 2017/0285023 A1 Oct. 5, 2017

Related U.S. Application Data

(63) Continuation-in-part of application No. 15/091,483, filed on Apr. 5, 2016.

(51) Int. Cl.
| | | |
|---|---|---|
| G01N 21/75 | (2006.01) | |
| G01N 33/564 | (2006.01) | |
| G01N 33/543 | (2006.01) | |
| G01N 33/558 | (2006.01) | |

(52) U.S. Cl.
CPC ........... *G01N 33/564* (2013.01); *G01N 21/75* (2013.01); *G01N 33/54386* (2013.01); *G01N 33/558* (2013.01); *G01N 2021/752* (2013.01); *G01N 2021/757* (2013.01)

(58) Field of Classification Search
None
See application file for complete search history.

(56) References Cited

U.S. PATENT DOCUMENTS

| | | |
|---|---|---|
| 3,620,677 A | 11/1971 | Morison |
| 3,811,840 A | 5/1974 | Bauer et al. |
| 3,888,629 A | 6/1975 | Bagshawe |
| 4,042,335 A | 8/1977 | Clement |
| 4,168,146 A | 9/1979 | Grubb et al. |
| 4,169,138 A | 9/1979 | Jonsson |
| 4,219,335 A | 8/1980 | Ebersole |
| 4,235,601 A | 11/1980 | Deutsch et al. |
| 4,258,001 A | 3/1981 | Pierce et al. |
| 4,313,734 A | 2/1982 | Leuvering |
| 4,348,207 A | 9/1982 | Cappel |
| 4,366,241 A | 12/1982 | Tom et al. |
| 4,435,504 A | 3/1984 | Zuk et al. |
| 4,446,232 A | 5/1984 | Liotta |
| 4,459,358 A | 7/1984 | Berke |
| 4,503,143 A | 3/1985 | Gerber et al. |
| 4,537,861 A | 8/1985 | Elings et al. |
| 4,594,327 A | 6/1986 | Zuk |
| 4,623,461 A | 11/1986 | Hossom et al. |
| 4,624,929 A | 11/1986 | Ullman |
| 4,632,901 A | 12/1986 | Valkirs et al. |
| 4,654,309 A | 3/1987 | Milnar et al. |
| 4,703,017 A | 10/1987 | Campbell et al. |
| 4,756,828 A | 7/1988 | Litman et al. |
| 4,770,853 A | 9/1988 | Bernstein |
| 4,803,170 A | 2/1989 | Stanton et al. |
| 4,806,311 A | 2/1989 | Greenquist |
| 4,855,240 A | 8/1989 | Rosenstein et al. |
| 4,857,453 A | 8/1989 | Ullman et al. |
| 4,861,711 A | 8/1989 | Friesen et al. |
| 4,868,108 A | 9/1989 | Bahar et al. |
| 4,916,056 A | 4/1990 | Brown, III et al. |
| 4,920,046 A | 4/1990 | McFarland et al. |
| 4,956,302 A | 9/1990 | Gordon et al. |
| 4,960,691 A | 10/1990 | Gordon et al. |
| 4,963,468 A | 10/1990 | Olson |
| 4,981,786 A | 1/1991 | Dafforn et al. |
| 4,999,285 A | 3/1991 | Stiso |
| 5,006,474 A | 4/1991 | Horstman et al. |
| 5,030,558 A | 7/1991 | Litman et al. |
| 5,039,607 A | 8/1991 | Skold et al. |
| 5,075,078 A | 12/1991 | Osikowicz et al. |
| 5,079,174 A | 1/1992 | Buck et al. |
| 5,120,504 A | 6/1992 | Petro-Roy et al. |
| 5,141,850 A | 8/1992 | Cole et al. |
| 5,164,294 A | 11/1992 | Skold et al. |
| 5,248,619 A | 9/1993 | Skold et al. |
| 5,356,782 A | 10/1994 | Moorman et al. |
| 5,753,497 A | 5/1998 | Bernstein et al. |
| 5,939,331 A | 8/1999 | Burd et al. |
| 6,485,982 B1 | 11/2002 | Charlton |
| 6,663,833 B1 * | 12/2003 | Stave ................. G01N 33/5302 422/110 |
| 9,377,458 B2 | 6/2016 | Plavina et al. |
| 2004/0214347 A1 * | 10/2004 | LaBorde .............. G01N 33/558 436/518 |
| 2004/0266025 A1 * | 12/2004 | Hickok .................. A61K 31/20 436/518 |
| 2006/0051358 A1 | 3/2006 | Banchereau et al. |
| 2010/0009389 A1 * | 1/2010 | Khan ............... G01N 33/54306 435/7.9 |
| 2012/0263796 A1 * | 10/2012 | Plavina ................ G01N 33/566 424/530 |
| 2013/0330724 A1 | 12/2013 | Chen et al. |
| 2013/0344621 A1 | 12/2013 | Wang et al. |
| 2015/0226758 A1 | 9/2015 | Grabert et al. |

OTHER PUBLICATIONS

Steenholdt et al., Clinical Implication of Measuring Drug and Anti-Drug antibodies by Different Assays hen Optimizing Infliximab Treatment failure in Crohn's Disease, The American Journal of Gastroenterology, May 6, 2014, pp. 1055-1064.*

(Continued)

*Primary Examiner* — Gary Counts (57) ABSTRACT

Portable devices for anti-drug antibodies (ADAs) testing are provided. These devices can be used in various applications, including but not restricted to the following: uniform testing of patients for ADAs; selection of therapeutic drug for patient treatment; evaluation of the need to change therapeutic drug or to apply tolerance regimens; selection of patients for clinical trials; comparison of therapeutic drugs marketed for a given disease and also gene therapy; scientific guidance for discovering therapeutic drugs; therapeutic drug development; postmarketing surveillance of therapeutic drugs.

19 Claims, 6 Drawing Sheets

(56) References Cited

OTHER PUBLICATIONS

Imaeda et al., Clinical utility of newly developed immunoassays for serum concentrations of adalimumab and anti-adalimumab antibodes in patients with Crohn's disease, J Gastroenterol,. 2014, 49, pp. 100-109.*
Barbosa, M. D. F. S. 2011 Immunogenicity of biotherapeutics in the context of developing biosimilars and biobetters. Drug Discovery Today 16: 345-353.
Barbosa, M. D. F. S. et al. 2012 Addressing drug effects on cut point determination for an anti-drug antibody assay. Journal of Immunological Methods 384: 152-156.
Barbosa, M. D. F. S. et al. 2013 Altering drug tolerance of surface plasmon resonance assays for the detection of anti-drug antibodies. Analytical Biochemistry 441: 174-179.
Barbosa, M. D. F. S. and Smith, D. D. 2014 Channeling postmarketing patient data into pharmaceutical regulatory systems. Drug Discovery Today 19: 1897-1912.
Kolata, G. When the immune system thwarts lifesaving drugs. The New York Times, May 15, 2017.
FDA approved label for TYSABRI (2004) TYSABRI (natalizumab) injection for use, 2004.
Barbosa, M.D.F.S. et al.Identification of the homologous beige and Chediak-Higashi syndrome genes. Nature 382, 262-265.

* cited by examiner

Chimeric antibody

Human antibody

PORTABLE DEVICES FOR DETECTION OF ANTIBODIES AGAINST THERAPEUTIC DRUGS

CLAIM OF PRIORITY

This is a continuation-in-part application and claims priority to U.S. patent application Ser. No. 15/091,483, filed on Apr. 5, 2016, which claims priority to U.S. Provisional Patent Application No. 62/146,232 filed on Apr. 10, 2015. The respective contents of these patent documents are hereby incorporated by reference in their entirety.

FIELD OF THE INVENTION

The present invention relates to devices for detection of antibodies against therapeutic drugs (ADAs), and their applications. More specifically, the present invention relates to portable devices that can be used for point-of-care testing and/or patient self-testing, and for deriving scientific knowledge in the fields of oncology, autoimmune diseases (including but not restricted to diabetes, multiple sclerosis and rheumatoid arthritis), cardiovascular diseases, rare diseases, and other diseases for which treatment comprises administration of a therapeutic drug and/or gene therapy.

BACKGROUND OF THE INVENTION

Therapeutic drugs (thereafter also referred to as "drug" or "drugs") can be either natural products, or small molecule drugs, or peptides, or therapeutic proteins (biotherapeutics), or small-molecule-biotherapeutic conjugates (Barbosa, M. D. F. S. et al. 2013 Anal. Biochem. 441: 174-179; Barbosa, M. D. F. S. and Smith, D. D. 2014 Drug Discov. Today 19: 1897-1912; Woodcock, J. et al. 2007 Nat. Rev. Drug Discov. 6: 437-442; all expressly incorporated by reference herein). Combination therapies (in which more than one entity is used) are also common.

In attempts to improve efficacy and/or to protect intellectual property positions, several new versions of marketed therapeutic drugs have been developed. In some instances, the novelty consists of introducing mutations to existing protein drugs. For example, new insulins are now available for treatment of diabetes, which contain mutated protein sequences relative to native insulin. Protein mutations may significantly alter the drug properties (including but not restricted to aggregation propensity), and may also create epitopes involved in T cell activation and unwanted anti-drug antibody (ADA) responses. Unwanted immunogenicity is also a concern for biosimilar versions of marketed protein drugs, typically requiring postmarketing surveillance (a biosimilar is a biotherapeutic similar to another one already marketed for which the patent has expired).

Despite attempts to standardize ADA detection across the pharmaceutical industry and to determine its impact, a holistic method for doing so is lacking. Unifying approaches to solve that challenge, as described in some embodiments of the present invention, have been non-obvious. That non-obviousness is exemplified by what has been for more than a decade the common practice of having language in the labels of biotherapeutics approved by Regulatory Agencies (such as the U.S. Food and Drug Administration—FDA), to the effect that it would be misleading to compare immunogenicity data amongst products, due to factors such as differences in assays, and lack of standardization of sample handling and collection (Barbosa, M. D. F. S. and Smith, D. D. 2014 Drug Discov. Today 19: 1897-1912; Expressly incorporated by reference herein). Those challenges are becoming increasingly complex, as a growing number of products are approved by regulatory agencies, including but not restricted to biosimilars and modified versions of marketed biotherapeutics. Although monitoring ADAs is typically a regulatory requirement for development and approval of protein drugs, it has been difficult to standardize and unify testing procedures for the drugs approved, including related biotherapeutics (different insulin versions are non-limiting examples). During the development of a biosimilar, the same assay may be used to test ADA for comparison of the biosimilar with the reference product, but typically there has been no systematic postmarketing comparison with the reference product. Also importantly, in other situations there have been no mechanisms in place to compare systematically therapeutic drugs approved for the same application regarding their immunogenicity in humans, and one of the difficulties is that the assays used may vary from one product to the other, and may be validated differently in various laboratories (Barbosa, M. D. F. S. and Smith, D. D. 2014 Drug Discov. Today 19: 1897-1912; expressly incorporated by reference herein).

Assays that detect known analytes have been widely used during pharmacokinetic studies (hereinafter "PK" assay). PK assays have been more amenable to standardization, as the positive control is representative of the analyte in the sample tested, allowing for quantification. On the contrary, ADA responses are typically polyclonal, and each sample contains an unknown ADA repertoire. Hence, there is no positive control that accurately reflects the analytes in the samples, and those ADA assays are qualitative. This further complicates comparison of immunogenicity of different biotherapeutics.

The present invention describes a novel portable device that addresses the need for standardization of ADA testing across various therapeutic drugs, and immunogenicity comparisons. Although Plavina et at. (U.S. Pat. No. 9,377,458; expressly incorporated by reference herein) describes a two-step bridging assay for the detection of anti-anti-VL4 antibodies, the labeled detection reagent in that assay is the drug itself. What follows is that the assay format used to test anti-anti-VL4 antibodies would require independent batches of labeled reagents for testing of different drugs, thus introducing concerns similar to the ones for existing assays, regarding comparing immunogenicity of biotherapeutics.

ADAs may negatively impact efficacy and/or safety of the drug (Barbosa, M. D. F. S. and Smith, D. D. 2014 Drug Discov. Today 19: 1897-1912; expressly incorporated by reference herein). Antibody responses against adalimumab and infliximab are non-limiting examples of ADAs that have been shown to decrease or abolish the efficacy of those therapeutic drugs. Adalimumab and infliximab are $IgG_1$ antibodies that differ regarding their variable region, although they both are tumor necrosis factor (TFN) blockers. It is typically not know if antibodies against the variable region of one of those two therapeutic drugs would cross-react with the other, or which one of those drugs is more immunogenic. Language in the labels of those therapeutic drugs (as approved by regulatory agencies) suggest that comparisons of the immunogenicity of either product would not be accurate, due to factors such as assay differences and sample handling (Barbosa, M. D. F. S. and Smith, D. D. 2014 Drug Discov. Today 19: 1897-1912; expressly incorporated by reference herein).

Hosts such as humans and test animals can also mount ADA responses against entities added to therapeutic proteins. For example, anti-polyethylene glycol (anti-PEG)

ADAs have been often observed when hosts are dosed with therapeutic drug-PEG conjugates (Barbosa, M. D. F. S. et al. 2013 Anal. Biochem. 441: 174-179; expressly incorporated by reference herein). Furthermore, the ADAs may be specific for drug degradation products.

A competent host immune system may mount unwanted responses to therapeutic drugs, such as the formation of neutralizing and/or non-neutralizing ADAs and/or various types of hypersensitivity (Barbosa, M. D. F. S. and Smith, D. D. 2014 Drug Discov. Today. 19: 1897-1912; expressly incorporated by reference herein). Host immune reactions often play an important role in adverse effects of therapeutic drugs. Various adverse reactions can result from the use of therapeutic drugs, for example life-threatening IgE- or IgG-mediated anaphylaxis or anaphylactic shock (Barbosa, M. D. F. S. and Smith, D. D. 2014 Drug Discov. Today. 19: 1897-1912; expressly incorporated by reference herein). Although immunogenicity may be associated with all drug classes, the main focus has been in immunogenicity of biologic drugs, likely due to their documented magnitude compared to immunogenicity of small molecules (Barbosa, M. D. F. S. and Smith, D. D. 2014 Drug Discov. Today. 19: 1897-1912; expressly incorporated by reference herein). ADAs may cause clinical syndromes ranging from mild hypersensitivity reactions to life-threatening responses, and may also decrease efficacy of the drug by directly neutralizing activity or by increasing drug clearance (Barbosa, M. D. F. S. and Smith, D. D. 2014 Drug Discov. Today. 19: 1897-1912; expressly incorporated by reference herein).

Antibodies (also named immunoglobulins) are proteins that bind a specific antigen. In mammals such as humans and mice, antibodies contain paired heavy and light polypeptide chains. Standard antibody structural units typically comprise a tetramer. Each tetramer is usually composed of two identical pairs of polypeptide chains, each pair having one "light" (typically having a molecular weight of about 25 kDa) and one "heavy" chain (typically having a molecular weight of approximately 50 kDa). "Isotype" as used herein is meant any of the subclasses of immunoglobulins. The known human antibody isotypes are IgG1, IgG2, IgG3, IgG4, IgA1, IgA2, IgM1, IgM2, IgD, and IgE.

Each antibody chain contains a variable and a constant region, as described above. The variable regions of the light and heavy chains are required for binding the target molecule (the antigen). All ADAs are capable of binding to a target molecule, and hence are referred to as binding antibodies.

An ADA that blocks or diminishes activity of the target protein is designated as a neutralizing antibody, commonly abbreviated to NAb. While some IgM can be neutralizing, usually most neutralizing ADAs (NAbs) are of the IgG type.

The following Igs are typically observed in higher mammals: IgD, IgA, IgE, IgM and IgG. IgD amounts to a small percentage of total serum Igs (less than 1%); IgA and IgM can comprise approximately 10-20%. IgG is the predominant Ig in blood. IgM is generally known as the early antibody, as it precedes the IgG response.

Host antibody responses against an antigen are typically polyclonal, comprising immunoglobulins that bind the antigen with various affinities and/or avidities. Hence, the assays used to detect antibody responses against therapeutic drugs are inherently qualitative, because there is no positive control antibody that would accurately represent all diverse antibodies in each of the samples collected from diverse sources and/or at various times following antigen exposure.

Another difficulty associated with monitoring ADAs for approved products is the cumbersome nature of collecting patient blood and shipping samples (commonly plasma or serum after blood processing) under special conditions to labs approved for such testing, and the lack of unified methodologies at such laboratories. In addition, such procedures are expensive and time-consuming, and in many instances laboratories offering those services are not even available and/or not known to physicians and/or patients. What follows is that there is an unmet need for devices to readily detect ADAs and to perform risk assessment for biotherapeutics. Such devices can have several utilities, including but not restricted to stratification of patients likely to benefit from a given therapy, comparison of similar products marketed for the same indication, guidance for new product development, tests during clinical trials, and post-marketing surveillance.

The difficulties associated with implementation of current approaches to postmarketing assessment of therapeutic drugs has been reviewed (Barbosa, M. D. F. S. and Smith, D. D. 2014 Drug Discov. Today 19: 1897-1912; expressly incorporated by reference herein). The US Food and Drug Administration recently initiated an active surveillance system ("the Sentinel Initiative"). However, one of the challenges associated with some aspects of drug comparisons with that system is that, in many cases, various different assays are used, resulting in data that is not amenable to the computational analysis. Such is the case for ADA assays.

With a plethora of therapeutic drugs being approved for the same indication, it is becoming increasingly complex for physicians and patients to select the medication likely to provide most benefits. For instance, several formulations of interferon-$\beta$ (IFN-$\beta$) are marketed (Rebif®, Betaseron®/Betaferon®, Avonex®, and Pelegridy®), and recently IFN-$\beta$ biosimilars are also being approved (Barbosa, M. D. F. S. and Smith, D. D. 2014 Drug Discov. Today 19: 1897-1912; expressly incorporated by reference herein). Devices to detect ADAs, as described in the present invention, would allow effective comparison of similar products marketed for the same indication, and/or to comparison of different products regarding suitability for specific patients.

ADA incidence against chronically administered products such as insulin and enzyme replacement therapies is also a concern. Even if the drug dosage is increased to compensate for NAbs, the chronic administration may result in immune complexes not being cleared, leading to immune complex disease and/or other syndromes (Barbosa, M. D. F. S. and Smith, D. D. 2014 Drug Discov. Today 19: 1897-1912; expressly incorporated by reference herein). In such cases, knowledge of ADA incidence and monitoring can provide an effective mechanism to evaluate risk and the need for tolerance induction regimens. Methods to assess risk of immune responses can also be useful to guide therapies other than the ones requiring chronic administration.

The present invention provides portable devices for evaluation of ADA responses against therapeutic drugs. Those devices can be used for one or more of the following: to stratify patients prior to therapy; to monitor efficacy of therapy; to monitor therapy safety; to guide discovery of novel therapeutic drugs; to guide therapeutic drug development; to estimate possibility of adverse events; to compare therapeutic drugs; to estimate need for tolerance induction; to empower doctors and patients regarding treatment decisions; for postmarketing surveillance.

BRIEF SUMMARY OF THE INVENTION

This invention is directed to devices to detect antibody responses against therapeutic drugs.

In one aspect, portable devices for ADA testing can be used by patients (self-test), at a point of care such as a physician's office, or in clinical trials, to detect antibodies against specific therapeutic drugs. In another aspect, the portable device can be used to test antibodies against a therapeutic drug in patients or animals, prior and/or after exposure to said drug. The therapeutic drug can be either a chemical entity, or a therapeutic protein (for example insulin or enzyme replacement therapies), or another entity, including but not restricted to antibodies and a combination of chemical entity and protein drug. Gene therapy is also within the scope of this application. In a further aspect, the portable ADA detection device can be used as a companion diagnostic.

In another aspect, the portable devices for ADA detection include an access code for a database.

The present invention provides devices that can be used for various applications, including but not restricted to the following: selection of therapeutic drug for patient treatment; evaluation of the need to change therapeutic drug or to apply tolerance regimens; selection of patients for clinical trials; comparison of therapeutic drugs marketed for a given disease; scientific guidance for drug discovery and/or development; postmarketing surveillance.

DETAILED DESCRIPTION OF THE INVENTION

Some embodiments of the present invention include devices to anticipate and detect host immune reactions against therapeutic drugs, and to perform risk assessment for those therapeutic entities. Those devices to detect antibodies against therapeutic drugs can enable self-testing and/or testing at a point of care such as at physician's office, hospital or emergency room. That information regarding the presence or absence of antibodies against the drug can be used independently or combined with, as a non-limiting example, data available in a database. In one embodiment, a code provided with the portable device allows access to a database.

Detection of Anti-Drug Antibodies (ADAs):

An embodiment of the present invention includes a device for detection of ADAs in body fluids (including but not restricted to blood and serum) and tissue samples. In another embodiment, antibodies bound to cells and/or various matrices can be detected. The described methods are not meant to constrain the present invention to any particular application or theory of operation. Rather, the provided methods are meant to illustrate generally that one or more portable devices can be used to detect ADA against therapeutic drugs, in the context of the holistic approach hereby proposed to standardize measurements.

In one embodiment, an application is described that provides a means of utilizing a portable device to detect ADAs for individual testing. Validation of the portable devices may include using them for tests with clinical samples, and comparison with other assays known in the art.

Assays known in the art for detection of ADAs may employ a variety of detection methods including but not limited to chromogenic, fluorescent, luminescent, or isotopic labels. Often those assays have multiple steps, may include washing steps, as well as special requirements for sample collection and preparation, and are not suitable for patient self-testing and/or point of care testing. Some assays known in the art are limited in scope to the detection of pre-defined antibodies, and are not suitable for samples with complex matrixes containing unknown antibodies with various affinities and/or avidities for the drug. In addition, ADA detection assays known in the art typically do not allow for valid comparisons amongst various biotherapeutics.

In one embodiment, the portable ADA testing device of the present invention may detect selected ADA isotypes. In another embodiment, the ADA assays of the present invention may comprise modifications to allow detection of all antibody isotypes. The testing devices may be tailored to detect individual samples or multiple samples. In another embodiment, the portable device may be used for antibody epitope mapping.

By "lateral flow" or "lateral flow technology" or "lateral flow assay" as used herein is meant a technology or assay based on the principle that the test substance and/or reagents flow in one (or more than one) direction, and may result in detection of a test substance. In another embodiment, lateral flow or vertical flow can be used. In another embodiment, the reactions of the portable ADA testing device can be performed without the above flow of reagents or samples (U.S. Pat. No. 4,219,335; expressly incorporated by reference herein).

None of the prior art utilizing lateral flow technology has identified the unifying devices and approach disclosed in embodiments of the present invention, for standardization of ADA measurements in the broad context of immunogenicity of therapeutic drugs, and across several therapeutic drugs. This is despite the fact that prior art on general principles of lateral flow technology dates of at least as early as 1971 (U.S. Pat. No. 3,620,677, which is incorporated herein by reference in its entirety). Additional non-limiting examples of patents disclosing lateral flow technology include the following US patent numbers, all incorporated by reference in their entirety herein: U.S. Pat. Nos. 3,811,840; 3,888,629; 4,042,335; 4,168,146; 4,169,138; 4,258,001; 4,313,734; 4,235,601; 4,366,241; 4,348,207; 4,446,232; 4,435,504; 4,459,358; 4,503,143; 4,537,861; 4,594,327; 4,624,929; 4,703,017; 4,632,901; 4,756,828; 4,999,285; 4,654,309; 4,623,461; 4,806,311; 4,861,711; 4,868,108; 4,770,853; 4,803,170; 4,960,691; 5,030,558; 4,857,453; 4,855,240; 4,920,046; 4,963,468; 4,981,786; 5,006,474; 4,916,056; 4,956,302; 5,039,607; 5,079,174; 5,120,504; 5,075,078; 5,164,294; 5,141,850; 5,248,619; 5,356,782; 5,939,331; 6,485,982; 9,377,458.

In another embodiment, the portable device of the present invention can detect ADAs by generating a signal other than colorimetric, for example electrochemiluminescence, or when an electrical property is altered upon binding of ADA (U.S. Pat. No. 4,219,335; expressly incorporated by reference herein). Said electrical property includes one or more of the following: resistance; impedance; capacitance; electrical potential. Other methods to detect a signal upon binding of sample ADAs can be employed for the construction of a unifying ADA testing portable device, and that is included within embodiments of the present invention. Capture of the ADAs alters the electronic property of the nanotube transistors. Carbon nanotube biosensors are also included within embodiments of the present invention.

In another embodiment, the device is used for detection of ADA in blood (U.S. Pat. Nos. 4,594,327; 5,939,331; 5,753, 497; all expressly incorporated by reference herein).

Non-limiting examples of modifications to increase sensitivity and accuracy of the portable device include optimization of the detection method and of sample collection and size, minimization of nonspecific background signal, optimization of materials used for device construction, optimization of reagent concentration immobilized on the device, selection of time for assay development and signal reading. In another embodiment, modifications are made to improve biophysical properties of the reagents used for the device cinstruction, comprising one or more of the following: stability, solubility, and oligomeric state. Improvements in device performance are included within embodiments of the present invention.

In another embodiment, the ADA-testing devices of the present invention contain information allowing access to the database. That information can be provided in various manners, for example, as a code on the device case, and/or in its interior, on a user manual, and/or on its packaging.

In another embodiment, various levels of security and access can applied to the database to be accessed using information provided with the portable device. As a non-limiting example, a device that that tests for ADAs against insulin may also contain a code allowing access to a section of a database that contains data pertaining to evaluation of efficacy or safety of insulin products, without allowing access for example to a section of the database that contains data pertaining to interferon-β. Those security levels and access can be changed if deemed appropriated. These examples are meant to illustrate the versatility of the related devices and databases, without constraining their use or construction.

The ADA-testing devices in one embodiment of the present invention may be compared for validation purposes with one or more conventional assay used for a given drug, such as for example a radioimmunoassay to test for antibodies against insulin or another assay relevant for comparisons. The parameters tested may include but are not limited to factors such as sensitivity, robustness, inter and intra assay variation, precision, sensitivity, matrix interference, cut point determination, minimal required dilution, and drug inhibition of the assay.

The ADA-testing devices of one embodiment of the present invention may be further validated in clinical and/or preclinical studies. That validation may include but not be restricted to comparison of data obtained with samples from the same humans or animal models, tested with an ADA-testing device of the present invention and another assay known in the art or newly invented. Other forms of ADA-testing device validation may also be used.

The ADA-testing devices of the present invention can be used alone to provide information of the ADA positive or negative status or can be is used in conjunction with a database and with statistical analyses to infer the probability of safety or efficacy issues due to ADA responses. Those uses are included in embodiments of the present invention.

In another embodiment, the ADA testing devices of the present invention can be used to guide selection of therapeutic drug dose. Therapeutic drug dose selection for humans has been typically made during phase 1 clinical trials, using a limited number of human subjects. ADAs that develops during the course of therapy can be an additional difficulty for selection of the correct dose of the corresponding therapeutic drug. When the ADAs are neutralizing, they can abolish drug efficacy, and higher drug concentrations may be required to counteract the ADA effects.

In another embodiment, the ADA testing device of the present invention and corresponding database can be used to select patients for clinical trials, including but not restricted to clinical development of novel biotherapeutics, biosimilars or biobetters.

By "pre-existing antibody" as used herein, is meant an antibody against a therapeutic drug or other entity that was present in the body of a human or animal prior to exposure to or administration of that therapeutic drug. In another embodiment, the device of the present invention can be used to test pre-existing antibodies in humans or animals. Data collected may be used for statistical analyses to investigate correlations.

Some examples are provided below. These examples are not to be construed as limiting.

Example 1

Portable Devices for Detection of Anti-Adalimumab Antibodies

Figure 1:
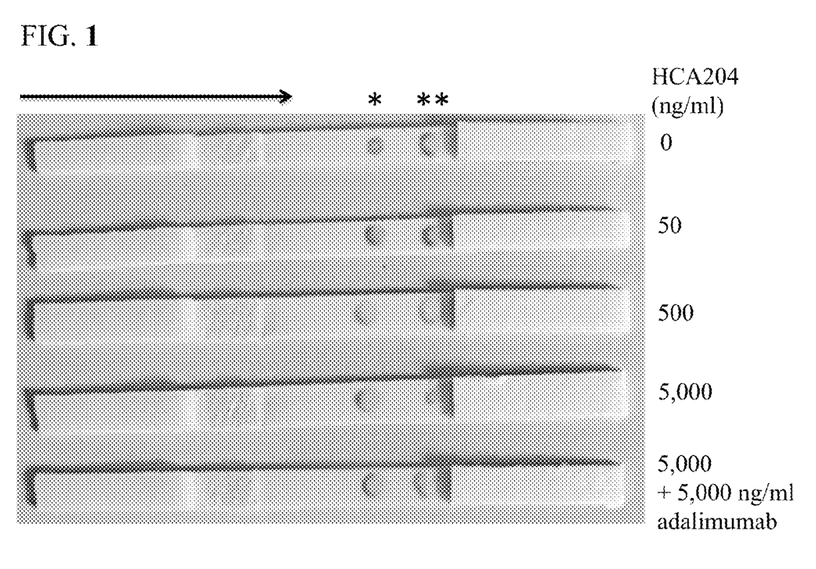
FIG. 1. Data obtained with a portable device that detects anti-drug antibodies (ADAs), with adalimumab as a capture reagent. The interior sections of this non-limiting example are shown. The test dot and control dots are indication by one or two asterisks, respectively. A human monoclonal anti-adalimumab antibody (HCA204) was loaded on the sample pad, binding to latex-labeled goat anti-human IgG on the conjugate pad, and subsequently to proteins immobilized on the membrane, generating a signal.

FIG. 1. Shows data obtained with a portable device that detects anti-drug antibodies (ADAs) against adalimumab. The interior sections of this non-limiting example are shown, and include of a sample pad, a conjugate pad, a membrane, and an absorbent pad, shown in that order from the left to the right. The conjugate pad was impregnated with a blue latex-labeled goat anti-human IgG polyclonal antibody. The control dot consisted of rabbit anti-goat IgG polyclonal antibody, immobilized on the membrane. The test dot consisted of a protein with sequence identical to adalimumab (Anti-hTNF-α-hIgG1; InvivoGen), hereinafter labeled as "adalimumab", immobilized on the membrane. A human monoclonal anti-adalimumab antibody (HCA204), was loaded on the sample pad, binding to latex-labeled goat anti-human IgG on the conjugate pad, and subsequently to proteins immobilized on the membrane, generating a signal. A horizontal arrow indicates the direction of liquid flow. The test dot and control dots are indicated by one or two asterisks, respectively. The concentrations of HCA204 loaded on each device are indicated to the right of the figure. A signal is observed in the absence of the test ADA (0 ng/ml of HCA204), suggesting unspecific binding.

Figure 2:
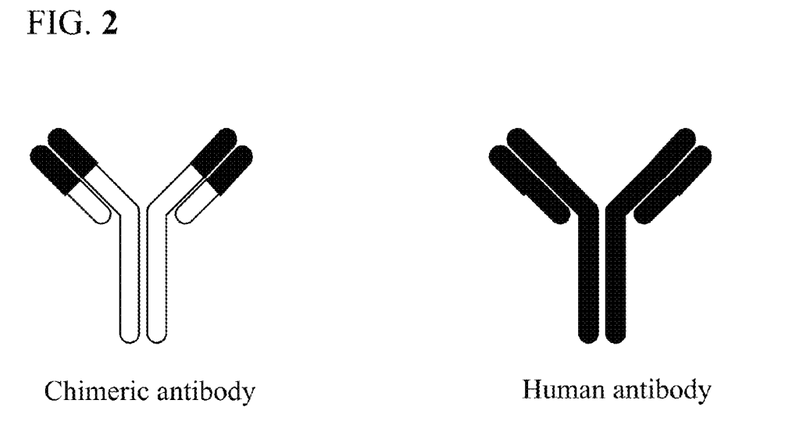
FIG. 2. Schematic representation of fully human (adalimumab) and chimeric (chimeric-adalimumab) antibodies.
Figure 3:
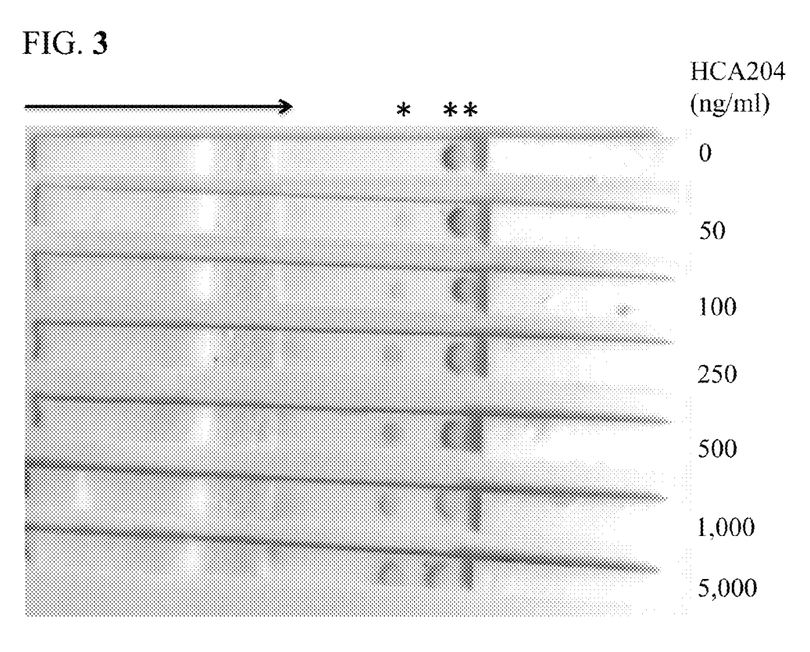
FIG. 3. Data obtained with a portable device that detects anti-drug antibodies (ADAs) against adalimumab, using a chimeric antibody as a capture reagent. A human monoclonal anti-adalimumab antibody (HCA204) was loaded on the sample pad, bound to latex-labeled goat anti-human IgG on the conjugate pad, and subsequently to proteins immobilized on the membrane, generating a signal. The test dot and control dots are indication by one or two asterisks, respectively.

To eliminate the unspecific binding seen in FIG. 1, an apparatus was devised, which uses a chimeric protein as capture reagent. FIG. 2 shows a schematic representation of a fully human adalimumab, and a chimeric antibody (Anti-hTNF-α-mIgG2a; InvivoGen), hereinafter labeled as "chimeric-adalimumab". The chimeric-adalimumab has a variable region, which has amino-acid sequence identical to adalimumab, fused to mouse IgG2a. FIG. 3 shows data obtained with a portable device that detects anti-drug antibodies (ADAs) against adalimumab, said device having chimeric-adalimumab immobilized on the membrane. The interior sections of this non-limiting example are shown, and include a sample pad, a conjugate pad, a membrane, and an absorbent pad, shown in that order from the left to the right. The conjugate pad was impregnated with a blue latex-labeled goat anti-human IgG polyclonal antibody. The control dot consisted of rabbit anti-goat IgG polyclonal antibody, immobilized on the membrane. The test dot consisted of chimeric-idalimumab immobilized on the membrane. A human monoclonal anti-adalimumab antibody (HCA204), which binds to the adalimumab variable region, was loaded on the sample pad. The latex-labeled goat anti-human IgG on the conjugate pad bound to HCA204, and subsequently to proteins immobilized on the membrane, generating a signal. A horizontal arrow indicates the direction of liquid flow. The test and control dots are indicated by one or two asterisks, respectively. The concentrations of HCA204 loaded on each device are indicated to the right of the figure. No signal was observed in the absence of HCA204, indicating specific binding.

Figure 4:
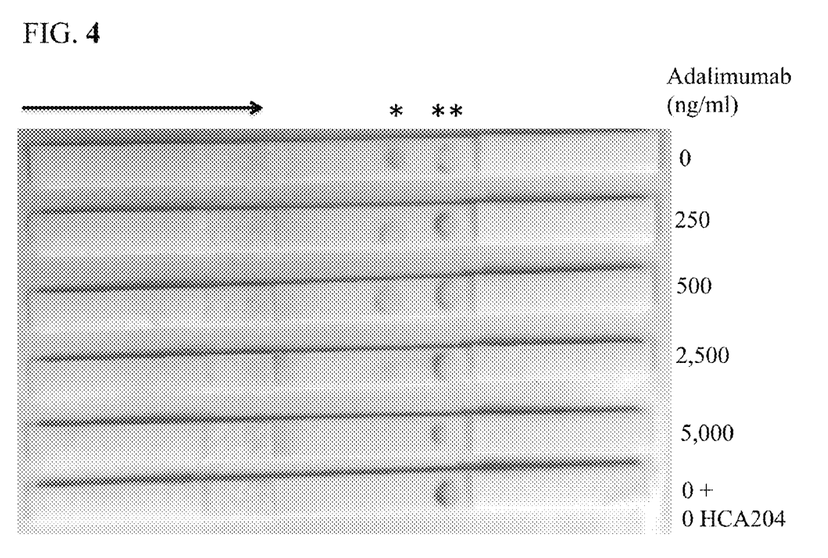
FIG. 4. Data obtained with a portable device that detects anti-drug antibodies (ADAs) against adalimumab, using a chimeric antibody as a capture reagent. A human monoclonal anti-adalimumab antibody (HCA204) was mixed with various concentrations of adalimumab, loaded on the sample pad, bound to latex-labeled goat anti-human IgG on the conjugate pad, and subsequently to proteins immobilized on the membrane, generating a signal. The test dot and control dots are indicated by one or two asterisks, respectively. The concentration of HCA204 on each sample was 250 ng/ml.

To further evaluate the specificity of the assay, the device of FIG. 3 (containing chimeric-adalimumab as a capture reagent) was tested following incubation of HCA204 with various concentrations of adalimumab. The reported affinity of HCA204 for adalimumab has been measured as $K_D=0.06$ nM (AbD Serotec, a Bio-Rad Company). FIG. 4 shows the reactivity of HCA204, after being mixed with various concentrations of adalimumab. A horizontal arrow indicates the direction of liquid flow. The test and control dots are indicated by one or two asterisks, respectively. The concentration of HCA204 on each sample was 250 ng/ml. The concentrations of adalimumab mixed with each HCA204 samples are indicated to the right of the figure. Inhibition of the assay by high concentrations of adalimumab further confirms specificity of the assay. A signal was still observed at concentrations of adalimumab 10-fold the one of the test antibody (HCA204).

Figure 5:
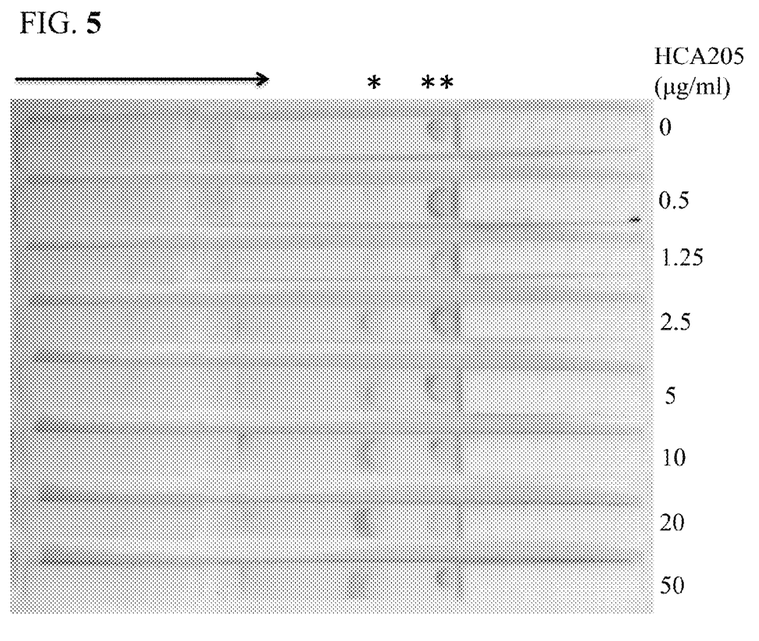
FIG. 5. Data obtained with a portable device that detects anti-drug antibodies (ADAs) against adalimumab, using a chimeric antibody as a capture reagent. A human monoclonal anti-adalimumab antibody (HCA205) was loaded on the sample pad, bound to latex-labeled goat anti-human IgG on the conjugate pad, and subsequently to proteins immobilized on the membrane, generating a signal. The test dot and control dots are indication by one or two asterisks, respectively.

FIG. 5 shows data obtained with a human anti-adalimimab monoclonal antibody (HCA205), using the portable device that detects anti-drug antibodies (ADAs) against adalimumab described in FIG. 2-4 above. The reported affinity of HCA205 for adalimumab has been measured as $K_D=10.5$ nM (AbD Serotec, a Bio-Rad Company). The interior of the device is shown. HCA205 was loaded on the sample pad, bound to latex-labeled goat anti-human IgG on the conjugate pad, and subsequently to proteins immobilized on the membrane, generating a signal. A horizontal arrow indicates the direction of liquid flow. The test and control dots are indicated by one or two asterisks, respectively. The concentrations of HCA205 loaded on each device are indicated to the right of the figure.

Example 2

Portable Device for Detection of Anti-Interferon-β Antibodies

Several IFN-β drugs are currently approved for the treatment of relapsing remitting multiple sclerosis (RRMS). Anti-IFN-β NAbs can affect the efficacy of those IFN-β drugs, but currently there are no regulatory requirements for systematic postmarketing monitoring of anti-IFN-β ADAs. A limited amount of data is typically used for the regulatory approval process. The decision-making process of what IFN-β to use is further complicated by the recent approval of IFN-β biosimilars and biobetters for RRMS treatment, with several similar drugs with the same mechanism of action now available. Those IFN-β formulations are administered at different doses and using different routes of administration (Barbosa, M. D. F. S. and Smith, D. D. 2014 Drug Discov. Today 19: 1897-1912; expressly incorporated by reference herein). In addition, if anti-IFN-β NAbs are present and cross react with an epitope common to all IFN-β, an increased dosage may be needed to counteract the NAb effect, or available alternative therapies (other than IFN-β) may need to be considered.

Figure 6:
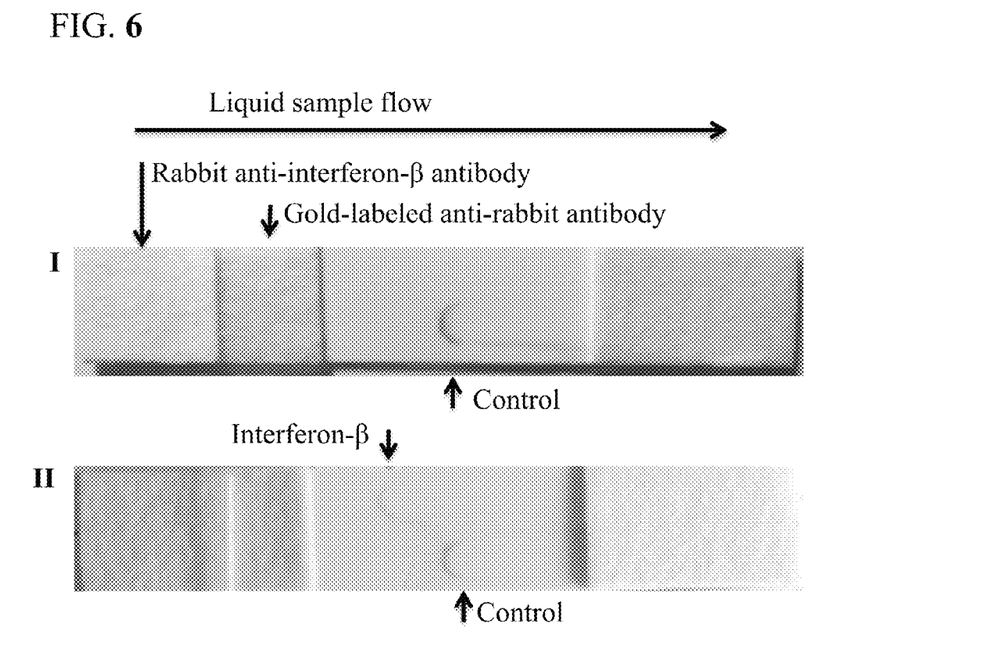
FIG. 6. Data obtained with a portable device that detects anti-drug antibodies (ADAs) against interferon-$\beta$. The interior sections of this non-limiting example are shown, and consist of a sample pad, a conjugate pad, a membrane and an absorbent pad. (I) Only the control was immobilized on the membrane, in the position indicated by the arrow; (II) Arrows indicate the signal in the positions where either interferon-$\beta$ or control were immobilized on the membrane.

FIG. 6 shows data obtained with a portable device that detects anti drug antibodies (ADAs) against interferon-β. The interior sections of this non-limiting example are shown, and consist of a sample pad, a conjugate pad, a membrane and an absorbent pad. The conjugate pad was impregnated with a goat gold-labeled anti-rabbit IgG polyclonal antibody. The control consisted of anti-goat IgG polyclonal antibody, immobilized on the membrane. When the sample (rabbit anti-interferon-β polyclonal antibody) is loaded on the sample pad, the liquid flows towards the conjugate pad, ADAs bind to gold-labeled antibodies, and the ADAs subsequently bind to the membrane-immobilized proteins in a selective manner, generating a signal. (I) Only the control was immobilized on the membrane, in the position indicated by the arrow; (II) Arrows indicate the signal in the positions where either interferon-β or control were immobilized on the membrane.

A patient or a caregiver (e.g. a physician or a nurse or other) using the portable device of the present invention to test for ADAs may also access a related database (with a code provided on the device, which may be embedded on the device itself or on its package or manual), to obtain information about one or more of the following: treatment options, correlations between human genetics and ADA development against specific biotherapeutics, presence of pre-exiting antibodies as a risk factor, incidence of ADAs against exiting drugs, comprehensive links to the scientific literature and/or to clinical trials. The information may guide decisions regarding the course of treatment with marketed drugs and/or guide patient selection for clinical trials, and/or suggest relevance of additional patient testing. It can also empower patients regarding their treatment. For example, if it is determined that a patient treated with a IFN-β drug has anti-IFN-β antibodies, and additional testing indicates that they are neutralizing, there would be a risk that ADA would be abrogating the efficacy of that drug for that specific patient. In that case, an alternative therapy option may be discussed. In another instance, if a newly diagnosed multiple sclerosis patient tests negative for pre-existing anti-IFN-β ADAs, that patient may be a candidate for IFN-β, and if genetic associations have been found in database analyses, patient genetic testing can further estimate the likelihood of ADA development during the course of IFN-β therapy. In addition, the portable device can be used at intervals during the course of therapy to monitor ADA incidence. The portable device of the present invention, when used at the physician's office, would become part of the patient records. Besides, it would be a standard assay, allowing reliable comparison between various drugs.

As demonstrated in Example 1, immobilization of a monoclonal antibody with a human constant region on the device membrane resulted in nonspecific signal (FIG. 1), because the labeled entity that binds to the human constant region of ADAs also binds to the human constant region of the antibody drug immobilized on the membrane. The amino acid sequence homology of the human IgG1 constant region on the membrane and constant regions of IgG ADAs is approximately 100%. What follows is that the signal is the same in the absence or presence of ADAs, and hence there is no functional assay. It precludes the use of this assay format to compare ADA responses against different monoclonal antibody drugs, which typically have a human constant region (Infliximab, Adalimumab and Natalizumab are non-limiting examples).

The concept tested in the present invention is that elimination of the unwanted binding of the labeled entity to a second entity immobilized on the membrane (in FIG. 1 said entity is the human constant region of a human antibody drug) would result in a functional assay. Variations in implementing that concept are possible and are within embodiments of the present invention. In cases when structural stability and/or other characteristics allow, removal of the region responsible for non-specific binding is possible, and are included within embodiments of the present invention. In FIG. 3, FIG. 4 and FIG. 5, a chimeric molecule was used, in which an entity, in that case said entity being the constant region of mouse IgG2a, replaced the human constant region of the drug, allowing for a functional assay. The amino acid sequence homology of the mouse IgG2a and human IgG1 constant regions is approximately less than 50%. Hence, the labeled entities, which in this case are labeled antibodies against the human IgG constant region, did not effectively bind to the immobilized mouse IgG2a constant region to result in a detectable signal. The binding propensity is estimated based on specific signal versus nonspecific signal (assay background). The same principles can also be used in creating chimeric proteins for assaying ADAs against drugs other than monoclonal antibody drugs; in that regard it is understood by one reasonably skilled in the art that mutations and substitutions or other protein engineering tools can be used to generate the chimeric proteins described in the present invention; they are included in embodiments of the present invention.

The invention claimed is:

1. A portable device comprising:
   a sample-receiving port adjacent to a sample-collecting pad;
   a conjugate pad comprising labeled antibodies capable of binding to a constant region of an anti-drug antibody; and
   a membrane comprising a capture agent comprising a chimeric protein comprising a therapeutic drug and a constant region of a different antibody;
   wherein the therapeutic drug is a variable region of a therapeutic antibody that is capable of binding to anti-drug antibodies that are specific to the therapeutic drug;
   wherein the constant region is from a different species than the species producing the anti-drug antibodies to be detected;
   wherein a sample contacted with the sample-collecting pad would laterally flow through the conjugate pad and subsequently to the membrane; and
   wherein the anti-drug antibodies are human anti-drug antibodies.

2. The portable device of claim 1, further comprising a filter positioned upstream from the sample-collecting pad.

3. The portable device of claim 1, further comprising a liquid reservoir positioned upstream from the sample-collecting pad.

4. The portable device of claim 1, further comprising a filter and a liquid reservoir positioned upstream from the sample-collecting pad.

5. The portable device of claim 1, wherein the constant region is a constant region from a non-human immunoglobulin.

6. The portable device of claim 1, wherein the membrane comprises two or more groups of capture agents, each group positioned at a different location on the membrane.

7. The portable device of claim 1, wherein the anti-drug antibodies are one or more of the antibody isotypes selected from the group consisting of IgG, IgM, and IgE.

8. The portable device of claim 1, wherein the labeled antibodies are capable of binding to anti-infliximab and anti-adalimumab antibodies.

9. The portable device of claim 1, wherein the capture agents comprise the variable regions of adalimumab or infliximab.

10. The portable device of claim 6, wherein the capture agents comprise either the variable region of adalimumab or the variable region of infliximab, wherein the capture agents comprising the variable region of adalimumab are positioned at a different location on the membrane than the capture agents comprising the variable region of infliximab.

11. A portable device for testing human anti-drug antibodies in tissues and body fluids, comprising:
   a sample-receiving port adjacent to a sample-collecting pad;
   a conjugate pad comprising labeled entities capable of binding to a constant region of a human anti-drug antibody; and
   a membrane comprising a capture agent comprising a chimeric protein comprising a therapeutic drug and a constant region of an antibody;
   wherein the therapeutic drug is capable of binding to human anti-drug antibodies that are specific to the therapeutic drug;
   wherein the constant region is from a different species than the species producing the anti-drug antibody to be detected; and
   wherein a sample contacted with the sample-collecting pad would laterally flow through the conjugate pad and subsequently to the membrane.

12. The portable device of claim 11, wherein the labeled entities are labeled antibodies.

13. The portable device of claim 11, wherein the therapeutic drug is an antibody.

14. The portable device of claim 11, wherein the therapeutic drug is a variable section of an antibody.

15. The portable device of claim 11, wherein the therapeutic drug is a natural product.

16. The portable device of claim 11, wherein the therapeutic drug is a small molecule drug.

17. The portable device of claim 11, wherein the therapeutic drug is a peptide.

18. The portable device of claim 11, wherein the therapeutic drug is a therapeutic protein.

19. The portable device of claim 11, wherein the therapeutic drug is a small-molecule-biotherapeutic conjugate.

* * * * *